United States Patent [19]

Sikora

[11] Patent Number: 5,121,746
[45] Date of Patent: Jun. 16, 1992

[54] ANAESTHETIC AND RESPIRATOR BREATHING CIRCUIT DEVICE

[76] Inventor: John R. Sikora, 850 Lancaster Drive, Kingston, Ontario, Canada, K7P 1R6

[21] Appl. No.: 707,023

[22] Filed: May 29, 1991

[51] Int. Cl.⁵ .............................................. A61M 15/00
[52] U.S. Cl. ................................ 128/203.12; 128/911; 128/912
[58] Field of Search ................ 128/202.27, 911, 912, 128/205.12, 203.12

[56] References Cited

U.S. PATENT DOCUMENTS

| 4,007,737 | 2/1977 | Paluch | 128/911 |
| 4,281,652 | 8/1981 | Miller | 128/911 |
| 4,391,271 | 7/1983 | Blanco | 128/205.12 |
| 4,463,755 | 8/1984 | Suzuki | 128/911 |
| 4,621,634 | 11/1986 | Nowacki et al. | 128/911 |
| 4,637,384 | 1/1987 | Schroeder | 128/911 |
| 4,967,744 | 11/1990 | Chua | 128/911 |

FOREIGN PATENT DOCUMENTS 1007540  3/1977  Canada.

Primary Examiner—Edgar S. Burr
Assistant Examiner—Aaron J. Lewis
Attorney, Agent, or Firm—Richard J. Hicks

[57] ABSTRACT

A simple flexible connector tube for use between an anaesthetic machine or a respirator is described. A flexible corrugated pipe is divided by an internal common wall into a larger and smaller flow passage and is provided with a bayonet type connector at the patient end and at least one of a quick release double friction fit connector at the machine end.

6 Claims, 3 Drawing Sheets

ANAESTHETIC AND RESPIRATOR BREATHING CIRCUIT DEVICE

FIELD OF THE INVENTION

This invention relates to an anaesthetic and respirator breathing circuit device, which is superior to prior art devices from the standpoint of convenience of operation and simplicity when used by a qualified medical practitioner.

BACKGROUND OF INVENTION

Numerous anaesthetic and respirator breathing apparatus devices have been suggested before and attention is particularly directed to Canadian Patent 1,007,540 issued Mar. 29, 1977 to James A. Bain and which forms the basis for virtually all such devices which are currently available on the market in North America. This device relies upon a pair of coaxially aligned tubes which are subject to kinking, internal disconnects, and relatively complicated hook-up devices. In contrast thereto the present invention provides an anaesthesia and respiratory system and a device which eliminates the use of separate tubes for the inlet and return circuits thus avoiding the hazard of an inner fresh gas tube which may separate during a surgical procedure. The physician no longer has to worry about fresh (feed) gas tube disconnects, and a simpler, more efficient and convenient method and apparatus for directing gas flows to and away from the patient, is provided.

The present device has certain other advantages such as ease of sterilization, light weight and length which is especially suited for surgical and critical care application. The present device also allows maximum humidity to the patient without the need of a water lock that may occlude the fresh gas flow, which is an important safety consideration.

The device of the present invention is also suited as a breathing circuit device on both paediatric and adult respirators, and minimizes circuit disconnections due to the design of the connectors. Further, the device can be easily pressure tested using a gas flow and a pressure gauge.

OBJECT OF INVENTION

Thus it is an object of the present invention to provide a simple, safe and inexpensive anaesthetic and respirator breathing apparatus which minimizes the risk of internal disconnects and has simple circuit disconnects.

BRIEF STATEMENT OF INVENTION

By one aspect of this invention there is provided a connector pipe for use in an anaesthetic or respirator machine between said machine and a patient face mask comprising:
 (a) a flexible tubular member, substantially circular in cross section, having an interior longitudinally extending dividing wall which divides said circular cross section into a larger and a smaller cross section so as to provide first and second fluid flow paths through said tubular member; and
 (b) means to connect said pipe to said face mask and to said anaesthetic or respirator machine.

BRIEF DESCRIPTION OF DRAWINGS

The embodiments of the present invention will now be described by way of example with reference to the accompanying drawings wherein:

Referring to FIG. 1 an anaesthetic system 7 includes an anaesthetic machine 8, a breathing bag 9, an adjustable pressure limiting valve 10, and a patient mask 11. A circuit adapter 12 is connected by a suitable bracket 13 to the anaesthetic machine 8 in a conventional manner. A three branch flexible plastic pipe 30 formed by outer flexible walls 21,22 with an intermediate flexible wall 25 provides separate fluid flow paths between the patient mask 11 at one end and the anaesthetic machine 8 and breathing bag 9 respectively at the other end.

Referring to FIG. 2 a respirator system 14 includes a respirator 15, an exhalation valve 16, a humidifier 17, and a patient mask 11. A conventional exhalation valve manifold 18 is connected by a suitable mounting arm 19 and bracket 20 to the respirator. The humidifier 17 is connected by a suitable bracket (not shown) to the respirator in a conventional manner. The three branch flexible pipe 30 provides separate fluid flow paths between the patient mask 11 at one end and the humidifier 17 and exhalation valve manifold 18 respectively at the other end as above.

Figure 1:
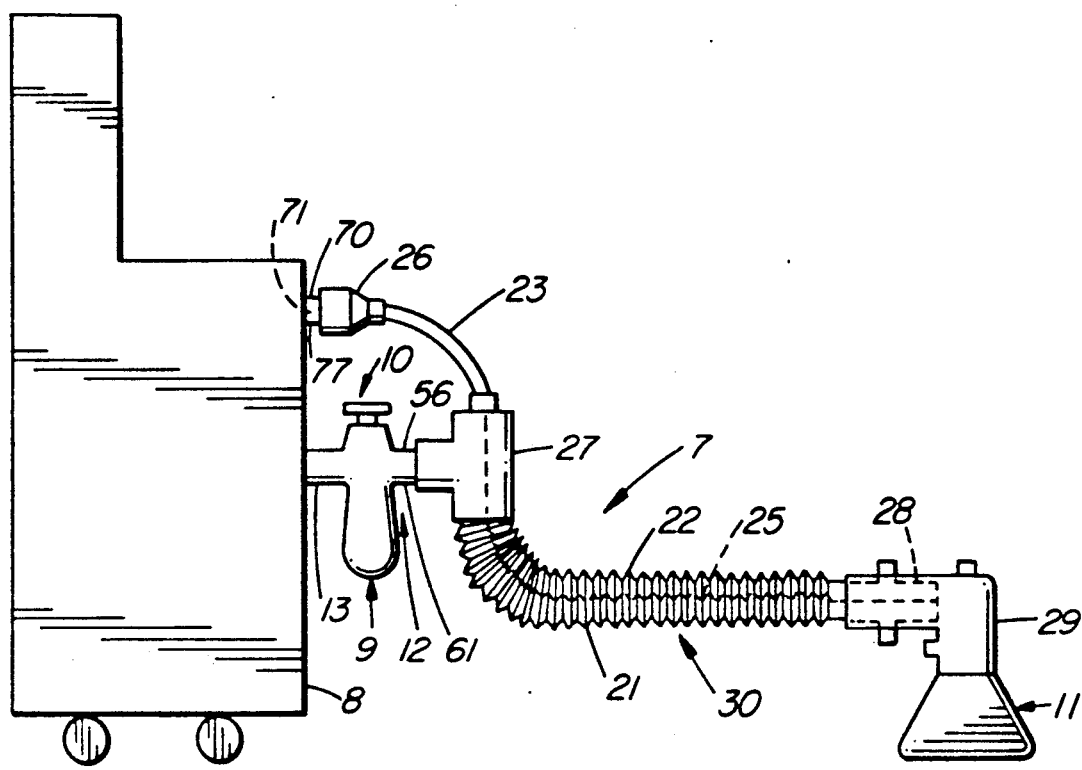
FIG. 1 is a schematic side view of an anaesthetic machine incorporating one embodiment of the present invention.
Figure 2:
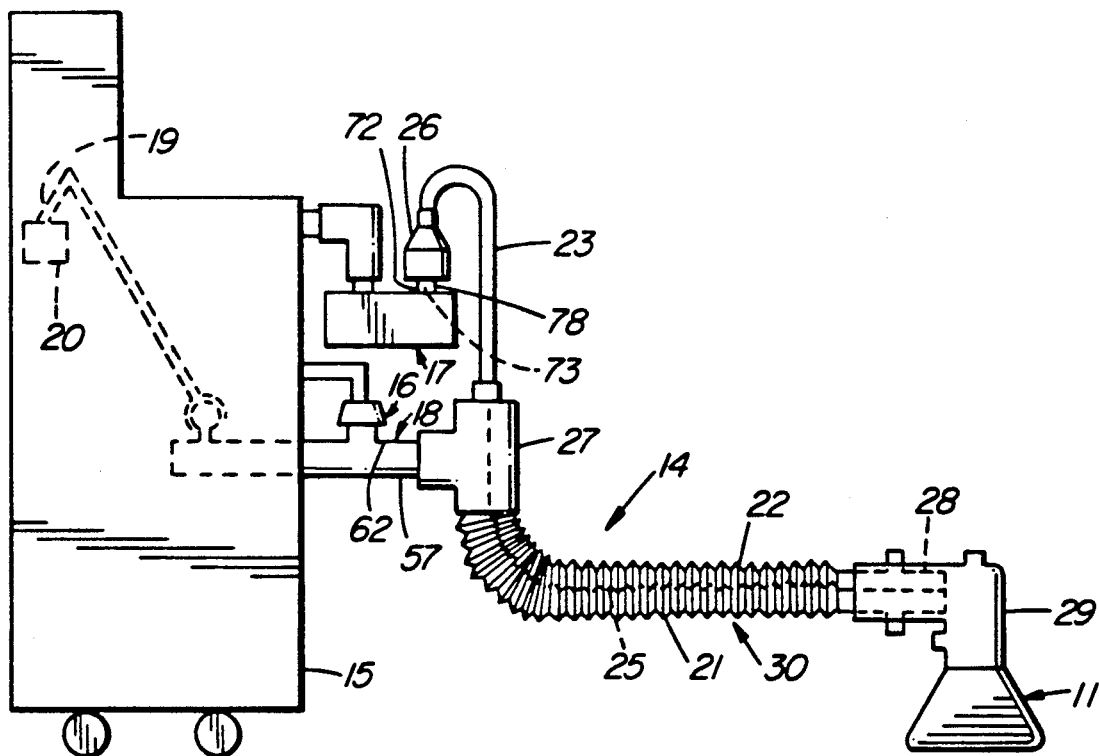
FIG. 2 is a schematic side view of a respirator system incorporating one embodiment of the present invention.

The walls 21, 22 and 25 of the three branch flexible pipes 30 are preferably formed from a material such as polyethylene. The members 21 and the tubular members 22 are preferably corrugated. A flexible connecting tubular member 23 connecting the pipe 30 to either the humidifier 17 or anaesthetic machine 8 need not be smooth walled as shown in FIGS. 1 and 2 but may be corrugated.

Figure 3:
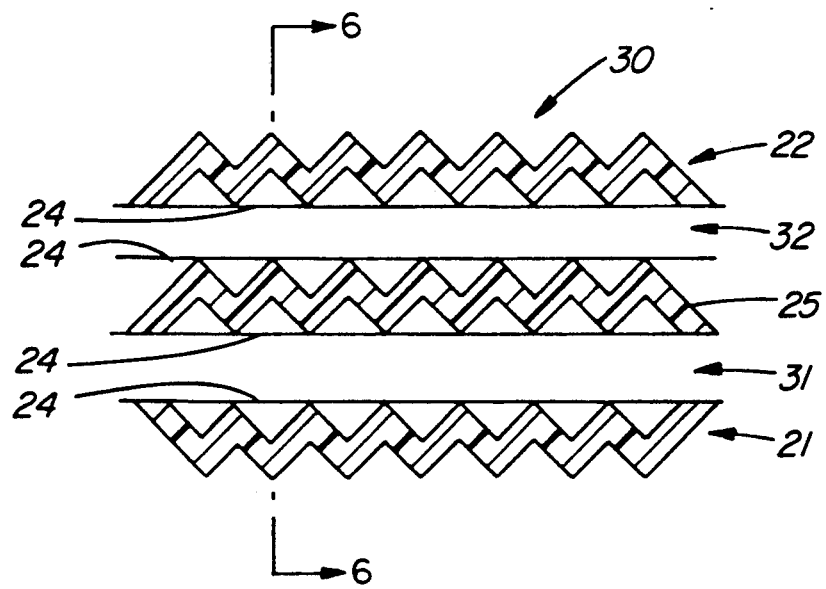
FIG. 3 is a sectional view of a portion of the pipe shown in FIGS. 1 and 2.

Longitudinal ribs 24 (FIG. 3) are integrally moulded to the inner surfaces of the three flexible walls 21, 22 and 25 to prevent disruption of gas flow in the event that a flexible tubular member collapses.

The pipe 30 is generally between 250 cm and 300 cm in length. The larger passage 31 formed between wall 21 and wall 25 and the smaller channel 32 formed between wall 22 and wall 25 are approximately 200 cm in length and the flexible connecting tubular member 23 is approximately 100 cm in length. The total internal volume of the larger passage 31 and the smaller passage 32 is approximately 90 ml per 30 cm of length.

This invention has been found suitable for all patients including paediatric patients. For paediatric patients under 10 kilograms, the pipe 30 is approximately 100 cm in length. The same configuration may be used as illustrated in FIGS. 1 and 2 whether the patient is attached to the anaesthetic machine 8 or the respirator 15 via pipe 30.

The pipe 30 is also suited for spontaneous continuous positive airway pressure off the anaesthetic machine 8 or the respirator 15.

Referring again to FIG. 1, the operative gas flow within the anaesthetic system 7 will be discussed. Nitrous oxide and oxygen flow from the anaesthetic machine 8 via the tube and passage connector 26, flexible connecting tubular member 23, tube and passage connector 27, passage 32, tube and passage connector 28 to passage connector 29 and so to the base of the patient mask 11 or directly to an endotracheal tube (not shown) and hence to a patient (not shown). During patient exhalation, the respiratory gases travel from the patient mask 11 or the endotracheal tube (not shown) through the passage connector 29 and the tube and passage connector 28, into passage 31 and the gases exit from the tube and passage connector 27 to the breathing bag 9, wherein the gases are conveyed through the pressure limiting valve 10 directly into the hospital pollution system (not shown).

Referring again to FIG. 2, the operative gas flow within the respirator system 14 will be discussed. An enriched gaseous mixture of oxygen flowing from the respirator 15 is conveyed via the humidifier 17, tube and passage connector 26, flexible connecting tubular member 23, tube and passage connector 27, smaller flexible tubular member 22, tube and passage connector 28 and the gases emanate from passage connector 29 to the base of the patient mask 11 or directly to the endotracheal tube (not shown) and hence to the patient (not shown). When the patient exhales, the respiratory gases travel from the patient mask 11 or the endotracheal tube through the passage connector 29 and the tube and passage connector 28, continuing down the interior of the larger flexible tubular member 21 and the gases exit from the tube and passage connector 27 to the exhalation valve manifold 18, wherein the gases are conveyed through the exhalation valve 16 to atmosphere.

Figure 4:
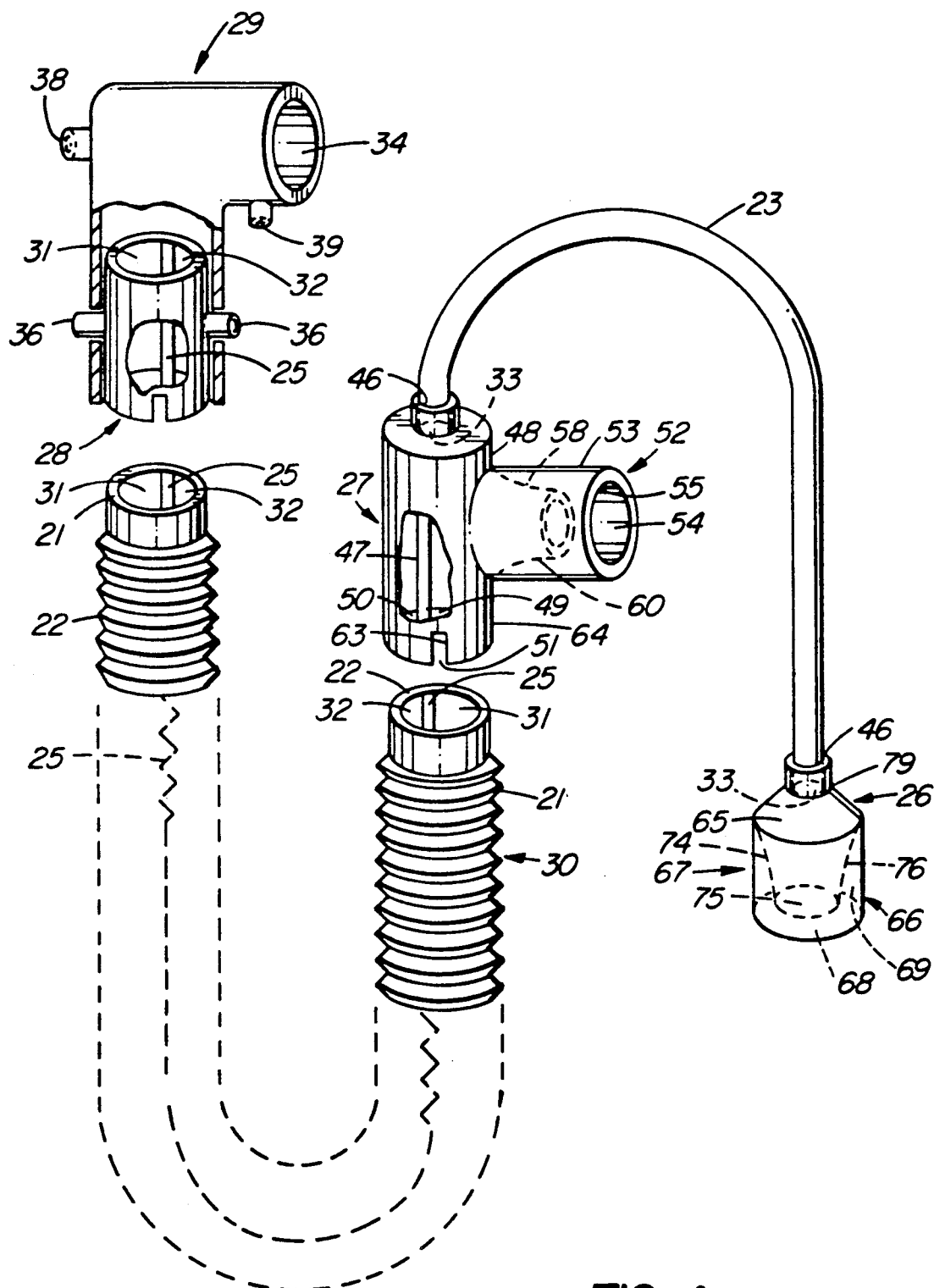
FIG. 4 is a perspective view, partly in section of a preferred embodiment of the pipe of present invention showing connections to mask and machine.

Referring to FIG. 4 which illustrate in greater detail a preferred embodiment of the invention in which the larger arced flexible corrugated wall moulded plastic tubular member 21 and the small arced flexible corrugated wall moulded plastic tubular member 22 are shown separated from tube and passage connectors 27 and 28 for clarity. The three branch flexible plastic pipe 30 comprises a larger arced flexible corrugated wall moulded plastic tubular member 21 integrally moulded to the small arced flexible corrugated wall moulded plastic tubular member 22 with a flexible interiorly disposed moulded plastic corrugated common wall 25, a circular flexible smooth walled extruded plastic tubular member 23, a first tube and passage connector 26, a second tube and passage connector 27, a third tube and passage connector 28, and a passage connector 29. The larger arced flexible corrugated wall moulded plastic tubular member 21 defining a first passage 31 has an arc length of about 40 mm and a chord length of about 22 mm. The smaller arced flexible corrugated wall moulded plastic tubular member 22 defining a second passage 32 has an arc length of about 29 mm and a chord length of about 22 mm. The circular flexible smooth walled extruded plastic tubular member 23 has an inside diameter of about 10 mm defining a third passage 33 and an outside diameter of 13 mm. The flexible interiorly disposed moulded plastic corrugated common wall 25 of the larger arced flexible corrugated wall moulded plastic tubular member 21 and the smaller arced flexible corrugated wall moulded plastic tubular member 22 has a thickness of about 1.5 mm.

The purpose of the flexible interiorly disposed moulded plastic corrugated common wall 25 is three-fold:
  (i) as a medium for heat transfer between the gases being transported within the first passage 31 and the second passage 32.
  (ii) as a strength and stability factor for the larger arced flexible corrugated wall moulded plastic tubular member 21 and the smaller arced flexible corrugated wall moulded plastic tubular member 22,
  (iii) to separate the first passage 31 from the second passage 32.

Figure 5:
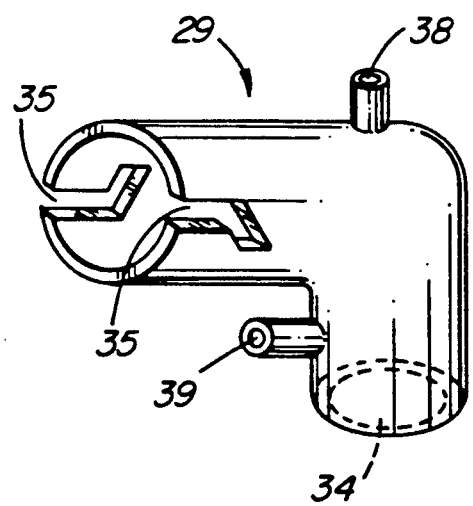
FIG. 5 is a sectional view of the mask connector of the present invention.
Figure 6:
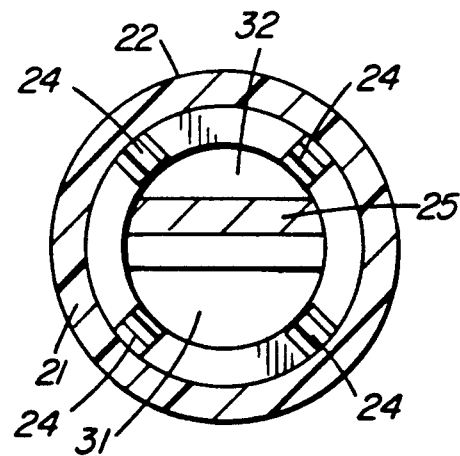
FIG. 6 is a cross section of the pipe of FIG. 3.

The passage connector 29 is a moulded plastic connector having an inside diameter of 15 mm and an outside diameter of 22 mm at the patient end to mate with the patient mask 11 or directly to the endotracheal tube (not shown), to define:
  (i) a single common passage 34 for communicating with the face mask 11 or the endotracheal tube,
  (ii) a pair of opposed slots 35 (FIG. 5) in the walls of the passage connector 29, which are arranged to interlock with a pair of protruding cylindrical pins 36 which are exteriorly disposed and integrally moulded to the outer surface 37 of the tube and passage connector 28, in conventional bayonet manner, and
  (iii) a temperature sensing port 38 for the insertion of a temperature sensor such as a thermistor or a thermometer (not shown) to monitor gas temperature and a pressure sensing port 39 for the insertion of a proximal airway pressure line (not shown) to monitor the patient's airway pressure in the proximity of the face mask 11 or the endotracheal tube.

The male tube and passage connector 28 at the patient end of the tube 30 includes a pair of protruding cylindrical pins 36 which are exteriorly disposed and integrally moulded to the outer surface 37 of the tube and passage connector 28.

The connector 28 may be connected to tube 30 by a solvent bond or other means (not shown).

The female tube and passage connector 27 composed of moulded plastic is mounted at the other end of pipe 30 as the other terminus of the passage 31 and the passage 32. The tube and passage connector 27 is also mounted at one end of the circular flexible smooth walled extruded plastic tubular member 23 as the terminus of the third passage 33. The female tube and passage connector 27 includes:
  (i) a partition 47 being interiorly disposed and integrally moulded to the inner surface 48 of the tube and passage connector 27. The partition 47 divides the tube and passage connector 27 into two distinct passage regions, a larger passage region defining a third passage means 49 and a smaller passage region defining a fourth passage means 50. The third passage means 49 extends through the tube and passage connector 27 to communicate the first passage 31 with the breathing bag 9 in the anaesthesia system 7 or the exhalation valve 15 in the respirator system 14. The fourth passage means 50 passes through the tube and passage connector 27 to connect the second passage 32 to the third passage 33.
  (ii) a slot 51 at one end of the tube and passage connector 27. This slot 51 follows a straight path through the walls of the tube and passage connector 27 and along the median of the partition 47 of the tube and passage connector 27, and, (iii) a double friction fitting adapter 52 comprising:
  (a) a first friction fitting adapter 53 composed of plastic which is integrally moulded to the tube and passage connector 27. The first friction fitting adapter 53 having an inside diameter of 22 mm defining a larger through passage 54 and an outside diameter of 25 mm. The larger through passage 54 forming an essential element of the third passage means 49. The inner surface 55 of the first friction fitting adapter 53 mates by a friction fit to the outer surface 56 of a conventional anaesthetic circuit adapter 12 (FIG. 1) or to the outer surface 57 or a conventional exhalation valve manifold 18 (FIG. 2), and,
  (b) a second friction fitting adapter 58 composed of plastic which is centrally positioned and integrally moulded to the inner surface 55 of the first friction fitting adapter 53. The second friction fitting adapter 58 having an inside diameter of 12 mm defining a smaller through passage 59 and an outside diameter of 15 mm. The smaller through passage 59 forming an essential element of the third passage means 49. The outer surface 60 of the second friction fitting adapter 58 extends step wise into a smaller outer annular surface slightly tapered to mate by a friction fit to the inner surface 61 of a conventional anaesthetic circuit adapter 12 (FIG. 1) or the inner surface 62 of a conventional exhalation valve manifold 18 (FIG. 2.

A coupling adapter (not shown) may be necessary depending on the type of non-conventional exhalation valve manifold used in the respirator system 14.

The pipe 30 may be fixed to a connector 27 by a solvent bond or other means (not shown). The circular flexible smooth walled extruded plastic tubular member 23 may be fixed to connector 27 by a solvent bond or other means 46.

Tube and passage connector 26 composed of moulded plastic is mounted at the other end of member 23, as the other terminus of the third passage 33. The connector 26 includes:

(a) a fifth passage means 65 extending through the tube and passage connector 26 to communicate the third passage 33 to a second gas source,
(b) a double friction fitting adapter 66 comprising:
  (i) an outer friction fitting adapter 67 composed of plastic which is integrally moulded to connector 26. Adapter 67 has an inside diameter of 22 mm defining a larger through passage 68 and an outside diameter of 25 mm. The larger through passage 68 forming an essential element of the fifth passage means 65. The inner surface 69 of the adapter 67 mates with the aid of a friction fit to the outer surface 70 of a conventional anaesthetic common gas outlet 61 (FIG. 1) or to the outer surface 72 of a conventional humidifier gas outlet 73 (FIG. 2), and,
  (ii) an inner friction fitting adapter 74 composed of plastic which is centrally positioned and integrally moulded to the inner surface 69 of adapter 67. The adapter 74 has an inside diameter of 12 mm defining smaller through passage 75 and an outside diameter of 15 mm. The smaller through passage 75 forming an essential element of the fifth passage means 65. The outer surface 76 of the fourth friction fitting adapter 74 extends step wise into a smaller outer annular surface slightly tapered to mate by a friction fit with the inner surface 77 of a conventional anaesthetic common gas outlet 71 (FIG. 1) or to the inner surface 78 of a conventional humidifier gas outlet 73 (FIG. 2).

A coupling adapter (not shown) may be necessary depending on the type of humidifier being used in the respirator system 14.

The tubular member may be fixed to inner surface 79 connector 26 by means of a solvent bond 46.

I claim:

1. A connector pipe for use in an anaesthetic or respirator machine between said machine and a patient face mask comprising:
  (a) a flexible tubular member, substantially circular in cross section, having an interior longitudinally extending substantially planar chordal dividing wall which divides said circular cross section into a larger and a smaller cross section so as to provide first and second fluid flow paths through said tubular member said planar chordal dividing wall being common to both said larger and said smaller cross sections; and
  (b) means to connect said pipe to said face mask and to said anaesthetic or respirator machine.

2. A connector pipe as claimed in claim 1 wherein said tubular member is a corrugated tubular member.

3. A connector pipe as claimed in claim 2 including longitudinal rib members moulded along an interior wall in said tubular member so as to provide a fluid flow path in the event that said tubular member is crushed.

4. A connector pipe as claimed in claim 1 wherein said means to connect said pipe to said face mask includes a bayonet type connection.

5. A connector pipe as claimed in claim 4 wherein said means to connect said pipe to either one of said anaesthetic machine and said respirator machine comprises at least one double friction fit connection.

6. A connection pipe as claimed in claim 5 wherein said means to connect said pipe to said anaesthetic or respirator machine includes two double friction fit connections.

* * * * *